United States Patent [19]

Bovenberg et al.

[11] Patent Number: 5,731,165
[45] Date of Patent: Mar. 24, 1998

[54] PROCESS FOR THE PRODUCTION OF 7-ADCA VIA EXPANDASE ACTIVITY ON PENICILLIN G

[75] Inventors: Roelof Ary Lans Bovenberg, Rotterdam; Bertus Pieter Koekman, Schipluiden; Dirk Schipper, Delft; Adrianus Wilhelmus Vollebregt, Naaldwijk, all of Netherlands

[73] Assignee: Gist-brocades, B.V., Ma Delft, Netherlands

[21] Appl. No.: 460,506

[22] Filed: Jun. 2, 1995

[51] Int. Cl.$^6$ .................. C12P 37/02; C12P 35/02; C07D 501/00
[52] U.S. Cl. .................. 435/47; 435/46; 435/51; 435/254.5; 540/218
[58] Field of Search .................. 435/51, 46, 47, 435/254.5, 320.1, 69.1, 252.3; 540/218

[56] References Cited

FOREIGN PATENT DOCUMENTS

| | | |
|---|---|---|
| 0 268 343 A2 | 2/1987 | European Pat. Off. . |
| 0 341 892 A1 | 11/1989 | European Pat. Off. . |
| 0 366 354 A2 | 5/1990 | European Pat. Off. . |
| 0 448 180 A2 | 9/1991 | European Pat. Off. . |
| 0 540 210 A1 | 10/1992 | European Pat. Off. . |
| 0 532 341 A1 | 3/1993 | European Pat. Off. . |
| WO 95/04148 | 2/1995 | WIPO . |
| WO 95/04149 | 2/1995 | WIPO . |

OTHER PUBLICATIONS

Baldwin et al., "The Enzymatic Ring Expansion of Penicillins To Cephalosporins: Side chain Specificity," *Tetrahedron* 43:3009–3017 (1987).

Cantwell et al., "Cloning and expression of a hybrid *Streptomyces clavuligerus* cefE gene in *Penicillium chrysogenum*," *Curr Genet* 17:213–221 (1990).

Yeh et al., "Biochemical characterization and Evolutionary Implication of β–Lactam Expandase/Hydroxylase, Expandase and Hydroxylase" *50 Years of Penicillin Application* (H. Kleinkauf and H. Von Döhren, Editors) pp. 209–210 (1991).

Aharonowitz, Y., et al. (1992) *Ann. Rev. Microbiol.* 46:461–495.

Baldwin, et al. (1988) *Natural Product Reports* 5(2):129–145.

Cantwell, et al. (1992) *Proc. R. Soc. Lond. B.* 248:283–289.

Coque, et al. (1993) *Mol. Gen. Genet.* 236:453–458.

Cortes, et al. (1987) *J. Gen. Microbiol.* 133:3166–3174.

Crawford, et al. (1995) *Bio/Technology* 13:58–61.

Ingolia, et al. (1989) *Med. Res. Rev.* 9:245–264.

Maeda, et al. (1995) *Enzyme and Microbial Technology* 17:231–234.

*Primary Examiner*—Robert A. Wax
*Assistant Examiner*—Daniel Mytelka
*Attorney, Agent, or Firm*—Morrison & Foerster LLP

[57] ABSTRACT

An overall process for the preparation and recovery of 7-aminodesacetoxycephalosporanic acid (7-ADCA) via enzymatic ring expansion activity on penicillin G, using a *Penicillium chrysogenum* transformant strain expressing expandase.

5 Claims, No Drawings

PROCESS FOR THE PRODUCTION OF 7-ADCA VIA EXPANDASE ACTIVITY ON PENICILLIN G

FIELD OF THE INVENTION AND DESCRIPTION OF THE PRIOR ART

The present invention concerns a biosynthetic process for preparation and recovery of 7-aminodesacetoxycephalosporanic acid (7-ADCA) .

β-Lactam antibiotics constitute the most important group of antibiotic compounds, with a long history of clinical use. Among this group, the prominent ones are the penicillins and cephalosporins. These compounds are naturally produced by the filamentous fungi *Penicillium chrysogenum* and *Acremonium chrysogenum*, respectively.

As a result of classical strain improvement techniques, the production levels of the antibiotics in *Penicillium chrysogenum* and *Acremonium chrysogenum* have increased dramatically over the past decades. With the increasing knowledge of the biosynthetic pathways leading to penicillins and cephalosporins, and the advent of recombinant DNA technology, new tools for the improvement of production strains and for the in vivo derivatization of the compounds have become available.

Most enzymes involved in β-lactam biosynthesis have been identified and their corresponding genes been cloned, as can be found in Ingolia and Quecener, Med. Res. Rev. 9 (1989), 245–264 (biosynthesis route and enzymes), and Aharonowitz, Cohen, and Martin, Ann. Rev. Microbiol. 46 (1992), 461–495 (gene cloning).

The first two steps in the biosynthesis of penicillin in *P. chrysogenum* are the condensation of the three amino acids L-5-amino-5-carboxypentanoic acid (L-α-aminoadipic acid) (A), L-cysteine (C) and L-valine (V) into the tripeptide LLD-ACV, followed by cyclization of this tripeptide to form isopenicillin N. This compound contains the typical β-lactam structure.

The third step involves the exchange of the hydrophillic side chain of L-5-amino-5-carboxypentanoic acid by a hydrophobic side chain by the action of the enzyme acyltransferase (AT). The enzymatic exchange reaction mediated by AT takes place inside a cellular organelle, the microbody, as has been described in EP-A-0448180.

Cephalosporins are much more expensive than penicillins. One reason is that some cephalosporins (e.g. cephalexin) are made from penicillins by a number of chemical conversions. Another reason is that, so far, only cephalosporins with a D-5-amino-5-carboxypentanoyl side chain could be fermented. Cephalosporin C, by far the most important starting material in this respect, is very soluble in water at any pH, thus implying lengthy and costly isolation processes using cumbersome and expensive column technology. Cephalosporin C obtained in this way has to be converted into therapeutically used cephalosporins by a number of chemical and enzymatic conversions.

The methods currently favoured in industry to prepare the intermediate 7-ADCA involve complex chemical steps leading to the expansion and derivatization of penicillin G. One of the necessary chemical steps to produce 7-ADCA involves the expansion of the 5-membered penicillin ring structure to a 6-membered cephalosporin ring structure (see for instance U.S. Pat. No. 4,003,894). This complex chemical processing is both expensive and noxious to the environment.

Consequently, there is a great desire to replace such chemical processes with enzymatical reactions such as enzymatic catalysis, preferably during fermentation. A key to the replacement of the chemical expansion process by a biological process is the central enzyme in the cephalosporin biosynthetic pathway, deacetoxycephalosporin C synthetase, or expandase.

The expandase enzyme from the bacterium *Streptomyces clavuligerus* was found to carry out, in some cases, penicillin ring expansions. When introduced into *P. chrysogenum*, it can convert the penicillin ring structure into the cephalosporin ring structure, as described in Cantwell et al., Proc. R. Soc. Lond. B. 248 (1992), 283–289. The expandase enzyme has been well characterized (EP-A-0366354) both biochemically and functionally, as has its corresponding gene. Both physical maps of the cefE gene (EP-A-0341892), DNA sequence and transformation studies in *P. chrysogenum* with cefE have been described.

Another source for a ring expansion enzyme is the bacterium *Nocardia lactamdurans* (formerly *Streptomyces lactamdurans*). Both the biochemical properties of the enzyme and the DNA sequence of the gene have been described (Cortés et al., J. Gen. Microbiol. 133 (1987), 3165–3174; and Coque et al., Mol. Gen. Genet. 236 (1993), 453–458, respectively).

Since the expandase catalyses the expansion of the 5-membered thiazolidine ring of penicillin N to the 6-membered dihydrothiazine ring of deacetoxycephalosporine C this enzyme would be of course a logical candidate to replace the ring expansion steps of the chemical process. Unfortunately, the enzyme works on the penicillin N intermediate of the cephalosporin biosynthetic pathway, but not on the readily available inexpensive penicillins as produced by *P.chrysogenum*, including penicillin G. Penicillin N is commercially not available and even when expanded, its D-aminoadipyl side chain cannot be easily removed by penicillin acylases.

It has recently been found that the expandase enzyme is capable of expanding penicillins with particular side chains to the corresponding 7-ADCA derivative. This feature of the expandase has been exploited in the technology as disclosed in EP-A-0532341, WO95/04148 and WO95/04149. In these disclosures the conventional chemical conversion of penicillin G to 7-ADCA has been replaced by the in vivo conversion of certain 6-aminopenicillanic acid (6-APA) derivatives in recombinant *Penicillium chrysogenum* strains containing an expandase gene.

More particularly, EP-A-0532341 teaches the in vivo use of the expandase enzyme in *P. chrysogenum*, in combination with a 5-carboxypentanoyl side chain as a feedstock, which is a substrate for the acyltransferase enzyme in *P. chrysogenum*. This leads to the formation of 5-carboxypentanoyl-6-APA, which is converted by an expandase enzyme introduced into the *P. chrysogenum* strain to yield 5-carboxypentanoyl-7-ADCA. Finally, the removal of the 5-carboxypentanoyl side chain is suggested, yielding 7-ADCA as a final product.

In WO95/04148 and WO95/04149 it has been disclosed that 3'-carboxymethylthiopropionic acid and 3,3'-thiodipropionic acid, respectively were found to be substrates for the expandase, yielding 2-(carboxyethylthio)acetyl- and 3-(carboxymethylthio)propionil-7-ADCA.

However, the process of the present invention provides more advantages, because of the high pen G synthese capacity of penicillin producing strains and the more favorable process of extraction of phenylacetyl-7-ADCA acid. Furthermore the phenylacetyl side chain of penicillin G is very amenable to enzymatic cleavage, by penicillin G amidases produced by several types of microorganisms yielding 6-APA, for instance separase G as disclosed in EP-A-0453047.

Various publications have reported the expandase not to accept penicillin G as a substrate for expansion (Baldwin & Abraham (1988), Natural Product Reports, 5(2), p.129–145; Maeda et al. (1995), Enzyme and Microbial Technology, 17, 231–234; Crawford et al. (1995), Bio/technology, 13, p.58–61).

Surprisingly, however, it has now been found that penicillin G producing *P.chrysogenum* transformed with an expandase encoding gene is capable of producing phenylacetyl-desacetoxycephalosporanic acid.

SUMMARY OF THE INVENTION

The present invention provides a process for the preparation and recovery of 7-aminodesacetoxycephalosporanic acid (7-ADCA) by:

a) transforming a *Penicillium chrysogenum* strain with an expandase gene, under the transcriptional and translational regulation of fungal expression signals;

b) fermenting said strain in a culture medium and adding to said culture medium phenylacetic acid or a salt or ester thereof suitable to yield penicillin G, which is expanded to form phenylacetyl-7-ADCA;

c) recovering the phenylacetyl-7-ADCA from the fermentation broth;

d) deacylating phenylacetyl-7-ADCA; and e) recovering the crystalline 7-ADCA.

Preferably, step (e) is a filtration step.

Preferably, phenylacetyl-7-ADCA is recovered from the fermentation broth by extracting the broth filtrate with an organic solvent immiscible with water at a pH of lower than about 4.5 and back-extracting the same with water at a pH between 4 and 10.

Moreover, a recombinant DNA vector comprising the DNA encoding expandase, functionally linked to the transcriptional and translational control elements of a fungal gene, for instance *Aspergillus nidulans* gpdA gene, and the *Aspergillus niger* glcA gene and host cells transformed with the same, are provided.

DETAILED DESCRIPTION OF THE INVENTION

The present invention concerns the use of functional gene constructs in *P. chrysogenum* for the in vivo expansion of the penicillin G ring structure to form a derivative of a key intermediate in the cephalosporin biosynthesis, 7-aminodesacetoxycephalosporanic acid, or 7-ADCA. This derivative has a chemical composition so as to allow efficient solvent extraction, thus providing an economically attractive recovery process.

Transformation of *P. chrysogenum* can, in principle, be achieved by different means of DNA delivery, like PEG-Ca mediated protoplast uptake, electroporation or particle gun techniques, and selection of transformants. See for example Van den Hondel en Punt, Gene Transfer and Vector Development for Filamentous Fungi, in: Applied Molecular Genetics of Fungi (Peberdy, Laten, Ogden, Bennett, eds.), Cambridge University Press (1991). The application of dominant and non-dominant selection markers has been described (Van den Hondel, supra). Selection markers of both homologous (*P. chrysogenum* derived) and heterologous (non-*P. chrysogenum* derived) origin have been described (Gouka et al., J. Biotechnol. 20 (1991), 189–200).

The application of the different transformant selection markers, homologous or heterologous, in the presence or absence of vector sequences, physically linked or not to the non-selectable DNA, in the selection of transformants are well known.

The ring-expansion reaction, mediated by the expandase enzyme is introduced into and expressed in this way in *P. chrysogenum*, for instance in strain Panlabs P14-B10, DS 18541 (deposited at CBS under accession number 455.95). It will be clear that in case the ring-expansion reaction is carried out in mutants thereof, the medium conditions have to be slightly adapted to obtain an efficient growth.

Furthermore, the cefE gene is placed under the transcriptional and translational control of fungal (be they filamentous or not) gene control elements, preferably derived of the *P. chrysogenum* IPNS gene, the β tubulin gene, the *Aspergillus nidulans* gpdA gene, or the *Aspergillus niger* glcA gene.

In summary, the present invention teaches how the activity of an expandase enzyme introduced into *P. chrysogenum* can be dedicated in vivo to the ring expansion of penicillin G.

In accordance with the present invention the β-lactam intermediate phenylacetyl-7-ADCA is produced in *P. chrysogenum* by adding phenylacetic acid or a salt or an ester thereof to the medium. Suitable salts are for instance those of sodium or potassium. 7-ADCA is efficiently recovered from the medium through a simple solvent extraction, for instance, as follows:

The broth is filtered and an organic solvent immiscible with water is added to the filtrate. The pH is adjusted in order to extract the cephalosporin from the aqueous layer. The pH range has to be lower than 4.5; preferably between 4 and 1, more preferably between 2 and 1. In this way the cephalosporin is separated from many other impurities present in the fermentation broth. Preferably a small volume of organic solvent is used, giving a concentrated solution of the cephalosporin, so achieving reduction of the volumetric flow rates. A second possibility is whole broth extraction at a pH of 4 or lower. Preferably the broth is extracted between 4 and 1 with an organic solvent immiscible with water.

Any solvent that does not interfere with the cephalosporin molecule can be used. Suitable solvents are, for instance, butyl acetate, ethyl acetate, methyl isobutyl ketone, alcohols like butanol etc.. Preferably butylacetate is used.

Hereafter the cephalosporin is back extracted with water at a pH between 4 and 10, preferably between 6 and 9. Again the final volume is reduced drastically. The recovery can be carried out at temperatures between 0° and 50° C., and preferably at ambient temperatures.

The aqueous cephalosporin solution thus obtained is treated with a suitable enzyme in order to remove the phenylacetyl side chain and obtain the desired 7-ADCA. A suitable enzyme for the same is the penicillin G acylase as described in EP-A-0453047, also named penicillin amidase.

Preferably, an immobilized enzyme is used, in order to be able to use the enzyme repeatedly. The methodology for the preparation of such particles and the immobilization of the enzymes have been described extensively in EP-A-0222462. The pH of the aqueous solution has a value of, for example pH 4 to pH 9, at which the degradation reaction of cephalosporin is minimized and the desired conversion with the enzyme is optimized. Thus, the enzyme is added to the aqueous cephalosporin solution while maintaining the pH at the appropriate level by, for instance, adding an inorganic base, such as a potassium hydroxide solution, or applying a cation exchange resin. When the reaction is completed the immobilized enzyme is removed by filtration. Another possibility is the application of the immobilized enzyme in a fixed or fluidized bed column, or using the enzyme in solution and removing the products by membrane filtration. Subsequently, the reaction mixture is acidified in the presence of an organic solvent immiscible with water.

After adjusting the pH to about 0.1 to 1.5, the layers are separated and the pH of the aqueous layer is adjusted to 2 to 5. The crystalline 7-ADCA is then filtered off.

The deacylation can also be carried out chemically as known in the prior art, for instance, via the formation of an iminochloride side chain, by adding phosphorus pentachloride at a temperature of lower than 10° C. and subsequently isobutanol at ambient temperatures or lower.

The following examples are offered by way of illustration and not by way of limitation.

EXAMPLE 1

Fermentative production of phenylacetyl-7-ADCA

*P. chrysogenum* strain Panlabs P14-B10, deposited at CBS under the accession number 455.95, is used as the host strain for the expandase expression cassette constructs.

The expression cassette used containing the expandase gene under the *P. chrysogenum* IPNS gene transcriptional and translational regulation signals is described in Crawford et al. (supra). Transformation and culturing conditions are as described in Crawford et al. (supra). Transformants are purified and analyzed for expression of the expandase enzyme by testing their capacity to produce adipoyl-7-ADCA as described by Crawford et al. (supra).

Adipoyl-7-ADCA producing transformants as for instance *P. chrysogenum* strain PC100, deposited with the ATCC under number 74185 are inoculated at 2.106 conidia/ml into a seed medium consisting of (g/l): glucose, 30; Pharmamedia (cotton seed meal), 10; Corn Steep Solids 20; $(NH_4)_2SO_4$, 20; $CaCO_3$, 5; $KH_2PO_4$, 0.5; lactose, 10; yeast extract, 10 at a pH before sterilisation of 5.6

The seed culture (20 ml in 250 ml Erlemeyer closed with a cotton plug) is incubated at 25° C. at 220 rpm. After 48 hours, 1 ml was used to inoculate 15 ml of production medium consisting of (g/l): $KH_2PO_4$, 0.5; $K_2SO_4$, 5; $(NH_4)_2SO_4$, 17.5; lactose, 140; Pharmamedia, 20; $CaCO_3$, 10; lard oil, 10 at a pH before sterilisation of 6.6.

After inoculation with the seed culture, 0.15–0.75 ml of 10% phenylacetic acid solution, adjusted to pH 7.0 with KOH, is added to the fermentation.

The production culture is inoculated at 25° C. at 220 rpm for 168 hours in a 250 ml Erlemeyer flask closed with a milk filter. Evaporated water is replenished every other day.

At the end of the production fermentation, the mycelium is removed by centrifugation or filtration and penicillin G and phenylacetyl-7-ADCA are analyzed by HPLC.

EXAMPLE 2

Analysis of phenylacetyl-7-ADCA production

Fermentation products from transformed Penicillium strains were analyzed by high performance liquid chromatography (HPLC). The HPLC system consisted of the following Spectra Physics components: P1500 solvent delivery system, AS 1000 injector, UV1000 variable wavelength detector (set at 214 nm) and a ISM 100 integrator or similar. The stationary phase was a Chrompack Chromspher C18 column. The mobile phase consisted of 75% phosphate buffer pH 2.6 and 25% acetonitril. The products were quantitated by comparison to a standard curve of phenylacetyl-7-ADCA and penicillin G. The identity of the phenylacetyl-7-ADCA was established by 600 MHz NMR of a deutero-chloroform solution obtained by acid extraction of the culture filtrate. The resonances of the phenylacetyl-7-ADCA in the acid extract proved to be identical with those of a synthetic sample.

We claim:

1. A method for making isolated phenylacetyl-7-aminodesacetoxy-cephalosporanic acid (phenylacetyl-7-ADCA) comprising the steps of:
   a) culturing a recombinant *Penicillium chrysogenum* strain in a culture medium containing phenylacetic acid, or a salt or ester;
   b) recovering phenylacetyl-7-ADCA from the culture medium; wherein said recombinant *Penicillium chrysogenum* strain is altered to contain the *Streptomyces clavuligerus* expandase gene, under the transcriptional and translational regulation of fungal expression signals, and said expandase gene encodes an expandase that can expand penicillin G to phenylacetyl-7-ADCA.

2. A process according to claim 1, wherein said recovery step (b) is performed by filtration, and by extracting the broth filtrate with an organic solvent immiscible with water at a pH lower than about 4.5 and back-extracting the extracted filtrate with water at a pH between 4 and 10.

3. The method of claim 1, further comprising the steps of:
   a) deacylating the recovered phenylacetyl-7-ADCA; and
   b) recovering 7-ADCA.

4. The method of claim 2, further comprising the steps of:
   a) deacylating the recovered phenylacetyl-7-ADCA; and
   b) recovering 7-ADCA.

5. The method according to claim 3, wherein said recovery step (b) is by filtration.

* * * * *